(12) United States Patent
Wong et al.

(10) Patent No.: US 10,702,622 B2
(45) Date of Patent: Jul. 7, 2020

(54) SYSTEM AND METHOD FOR APPLICATION CONTROLLED FRAGRANCE GENERATION

(71) Applicant: Intel Corporation, Santa Clara, CA (US)

(72) Inventors: Hong W. Wong, Portland, OR (US); Jiancheng Tao, Shanghai (CN); Vivek M. Paranjape, Hillsboro, OR (US); Cheong W. Wong, Beaverton, OR (US); Xiaoguo Liang, Shanghai (CN); Wah Yiu Kwong, Hillsboro, OR (US); Shaorong Zhou, Shanghai (CN); Russell S. Beauregard, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 441 days.

(21) Appl. No.: 15/534,750

(22) PCT Filed: Dec. 10, 2014

(86) PCT No.: PCT/CN2014/093432
§ 371 (c)(1),
(2) Date: Jun. 9, 2017

(87) PCT Pub. No.: WO2016/090564
PCT Pub. Date: Jun. 16, 2016

(65) Prior Publication Data
US 2017/0340764 A1 Nov. 30, 2017

(51) Int. Cl.
*A61L 9/03* (2006.01)
*H04M 1/21* (2006.01)
*H04M 1/725* (2006.01)

(52) U.S. Cl.
CPC .............. *A61L 9/035* (2013.01); *A61L 9/03* (2013.01); *H04M 1/21* (2013.01); *A61L 2209/11* (2013.01);
(Continued)

(58) Field of Classification Search
None
See application file for complete search history.

(56) References Cited

U.S. PATENT DOCUMENTS 6,390,453 B1 * 5/2002 Frederickson ........ A61M 15/02
261/100
8,061,628 B1 * 11/2011 Kvietok .............. A01M 1/2033
239/34

(Continued)

FOREIGN PATENT DOCUMENTS

CN 1484163 3/2004
CN 101459709 6/2009
(Continued)

OTHER PUBLICATIONS

International Bureau, "International Preliminary Report on Patentability," issued in connection with international patent application No. PCT/CN2014/093432, dated Jun. 22, 2017, 6 pages.
(Continued)

*Primary Examiner* — Thor S Campbell
(74) *Attorney, Agent, or Firm* — Hanley, Flight & Zimmerman, LLC

(57) ABSTRACT

A system and method for application controlled fragrance generation are disclosed. A particular embodiment includes: receiving a fragrance trigger from an application, the fragrance trigger being associated with a particular fragrance that corresponds to an event, action, image, sound, or gesture depicted in the application, determining a temperature needed to cause the particular fragrance to be emitted
(Continued)

from a fragrance cartridge; and causing a thermal element to heat the fragrance cartridge to the determined temperature.

20 Claims, 6 Drawing Sheets

(52) U.S. Cl.
CPC .... *A61L 2209/111* (2013.01); *H04M 1/72522* (2013.01)

(56) References Cited

U.S. PATENT DOCUMENTS

| | | | | |
|---|---|---|---|---|
| 2004/0265164 | A1* | 12/2004 | Woo | A01M 1/2033 422/5 |
| 2005/0185392 | A1* | 8/2005 | Walter | A61L 9/037 362/96 |
| 2006/0154642 | A1* | 7/2006 | Scannell, Jr. | A01G 9/02 455/404.1 |
| 2006/0261179 | A1* | 11/2006 | Davies | A01M 1/2044 239/34 |
| 2008/0085103 | A1* | 4/2008 | Beland | A61L 9/035 392/390 |
| 2009/0073694 | A1* | 3/2009 | Scannell, Jr. | A47G 7/06 362/253 |
| 2010/0243754 | A1* | 9/2010 | Harris | A01M 1/2033 239/34 |
| 2012/0121813 | A1* | 5/2012 | Wang | B41J 11/0015 427/401 |
| 2014/0377130 | A1* | 12/2014 | Edwards | A61L 9/02 422/5 |
| 2015/0048178 | A1* | 2/2015 | Edwards | A61L 9/032 239/13 |
| 2015/0217921 | A1* | 8/2015 | On | B65D 75/5855 206/460 |
| 2016/0363917 | A1* | 12/2016 | Blackley | G05B 19/042 |
| 2017/0020188 | A1* | 1/2017 | Cameron | H04L 67/025 |

FOREIGN PATENT DOCUMENTS

| | | |
|---|---|---|
| CN | 102158603 | 8/2011 |
| CN | 103475938 | 12/2013 |
| CN | 103685653 | 3/2014 |
| JP | 2002359671 | 12/2002 |
| JP | 2009212891 | 9/2009 |
| WO | 2016090564 | 6/2016 |

OTHER PUBLICATIONS

Patent Cooperation Treaty, "Notification of Transmittal of the International Search Report and the Written Opinion of the International Searching Authority," issued in connection with International Patent Application No. PCT/CN2014/093432, dated Sep. 2, 2015, 3 pages.

Patent Cooperation Treaty, "International Search Report," issued in connection with International Patent Application No. PCT/CN2014/093432, dated Sep. 2, 2015, 5 pages.

Patent Cooperation Treaty, "Written Opinion," issued in connection with International Patent Application No. PCT/CN20141093432, dated Sep. 2, 2015, 4 pages.

\* cited by examiner

SYSTEM AND METHOD FOR APPLICATION CONTROLLED FRAGRANCE GENERATION

TECHNICAL FIELD

This patent application relates to electronic systems, computing devices, mobile devices, and computer-implemented software, according to various example embodiments, and more specifically to a system and method for application controlled fragrance generation.

BACKGROUND

There are printed materials, such as scratch-and-sniff stickers, that incorporate encapsulated aromas designed to generate a scent when a user rubs an image. This technology has been used in a wide variety of books, magazines, and advertisements although most popular use has been in children's books. In social sciences, scent generation opens the possibility of forming memories, triggering responses, and eliciting emotion. For humans and many animals, olfaction is one of the primary sensory inputs that can be used to draw attention, create interest, and enhance engagement. This makes scent generation technologies useful for a wide variety of purposes including more realistic immersive experiences, eliciting conditioned responses, entertainment, advertising, and education. For example, scent features can complement future digital textbooks and mobile interactive education applications targeted at improving student engagement and learning outcomes.

Current computer-based applications and games played on computers or a gaming platform employ the same advanced graphics and sound qualities found in film or video. These technologies create an audiovisual experience that immerses the user in a film or game like never before, stimulating sight, sound and even tactile sensations through deep bass vibrations provided by subwoofers and tactile feedback provided by some game controllers. There remains, however, one form of sensory perception that is not stimulated—the sense of smell.

Numerous prior art systems have attempted to provide a scent to the environment that compliments or correlates to an audiovisual stimulus. Examples include the smell of burning rubber coordinating with the screech of tires, or the scent of flowers when a corresponding image appears. Prior art systems have primarily been directed to introducing fragrances to large environments, such as an entire theater. These systems have by and large suffered from the problem that a fragrance will linger long after the coordinating audiovisual input has changed, and may in fact be difficult to replace with another scent as the scenes change. None of these prior art devices, however, provide a useful and commercially viable system for fragrance delivery to enhance an audiovisual presentation.

BRIEF DESCRIPTION OF THE DRAWINGS

The various embodiments are illustrated by way of example, and not by way of limitation, in the figures of the accompanying drawings in which.

DETAILED DESCRIPTION

In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, a system and method for application controlled fragrance generation are disclosed. The example embodiment includes a fragrance generator coupled with a controller and a software-controllable switch for activating the fragrance generator. The controller can be triggered to activate the switch and the fragrance generator by an application program running on a computing platform or mobile device. The controller can also be triggered to activate the switch and the fragrance generator by inputs from various sensor devices, such as imaging devices (e.g., cameras), audio devices (e.g., voice or speech recognition devices), infrared control devices, wireless devices (e.g., WiFi, Bluetooth, Bluetooth Low Energy, RFID, NFC), and the like. WiFi or Wi-Fi is a local area wireless technology that allows an electronic device to exchange data or connect to the internet using UHF or super high frequency (SHF) radio waves. Bluetooth is a wireless technology standard for exchanging data over short distances using short wavelength, ultra-high frequency (UHF) radio waves. Radio frequency identification (RFID) is a well-known technology for the wireless non-contact use of radio-frequency electromagnetic fields to transfer data, for the purposes of automatically identifying and tracking tags attached to objects, for example. Near-field or near field communication (NFC) is a form of short-range wireless communication where the antenna used is much smaller than the wavelength of the carrier signal. WiFi, Bluetooth. Bluetooth Low Energy, RFID, and NFC technologies are well-known to those of ordinary skill in the art.

In a particular embodiment, a fragrance cartridge of the fragrance generator can be configured to conform to the form factor of a Secure Digital (SD) card. Secure Digital (SD) is a nonvolatile memory card used extensively in portable devices, such as mobile phones, digital cameras, global positioning satellite (GPS) navigation devices, handheld consoles, tablet computers, and the like. The fragrance cartridge, configured as an SD card, can be inserted into a standard SD card slot on a computing platform or mobile device. It will be apparent to those of ordinary skill in the art that the fragrance cartridge can be configured in different form factors as well.

Figure 1:
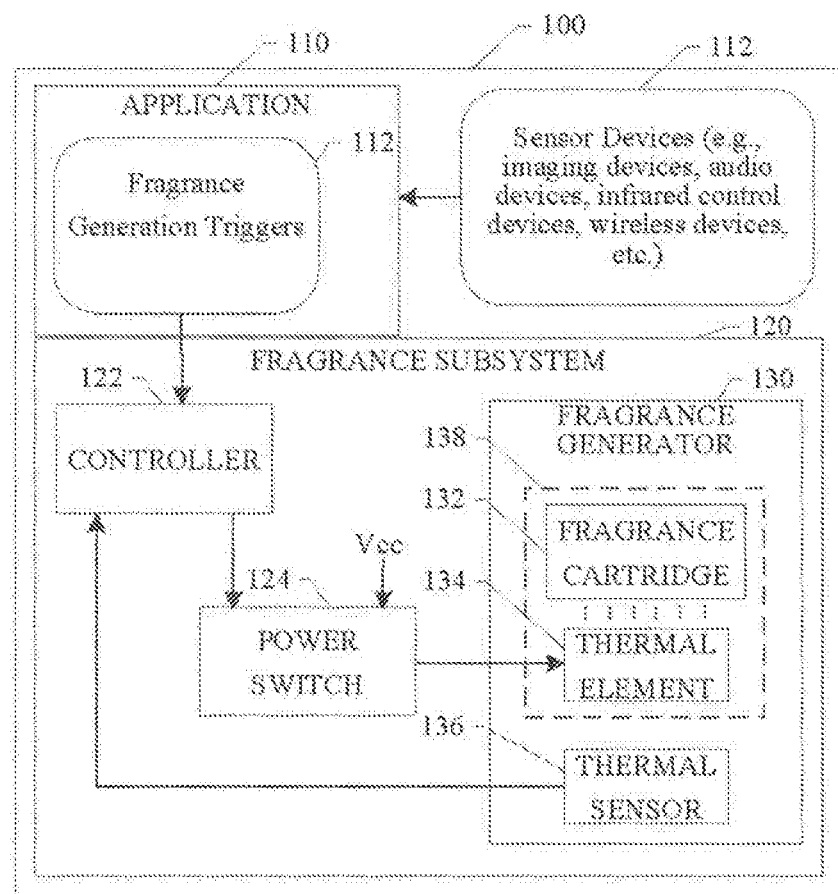
FIG. 1 illustrates an example embodiment of a system for application controlled fragrance generation.

FIG. 1 illustrates an example embodiment of a system for application controlled fragrance generation. Referring now to FIG. 1, an example embodiment 100 described herein is configured to provide an application 110 running in a software execution environment provided by a computing platform 100 of an example embodiment. The computing platform 100 may be a personal computer (PC), a laptop computer, a tablet computing system, a Personal Digital Assistant (PDA), a cellular telephone, a smart phone, a web appliance, a set-top box (STB), a game console, or any machine capable of executing a set of instructions (sequential or otherwise) or activating processing logic that specifies actions to be taken by that machine. The computing platform 100 of an example embodiment can include one or more sensor devices 112, such as imaging devices (e.g., cameras), audio devices (e.g., voice or speech recognition devices), infrared control devices, wireless devices (e.g., WiFi, Bluetooth, Bluetooth Low Energy, RFID, NFC), and the like. The application 110 can use input provided by the sensor devices 112 and/or internal programming processes to generate fragrance generation triggers that cause a fragrance subsystem 120 to activate and emit a selected fragrance. The fragrance generation triggers can be caused by a particular image, a voice command, a user gesture, or a command or input sent from the sensor devices 112. The fragrance generation triggers in an example embodiment can be implemented as data objects or messages conveyed from the application 110 to the fragrance subsystem 120 using standard data transmission mechanisms. As described in more detail below, the generation and transmission of the fragrance generation triggers and the resulting emission of a selected fragrance can be controlled by the application 110 to coincide with events, actions, imagery, sounds, or gestures depicted in the application 110. In this manner, the system 100 can enhance a user experience in the application 110 by selectively and synchronously causing an olfactory stimulus to be provided to a user in combination with the other stimuli provided by the application 100 and other subsystems of system 100.

Referring still to FIG. 1, the system 100 includes a fragrance subsystem 120. In an example embodiment, the fragrance subsystem 120 includes a controller 122, a software-controllable switch 124, and a fragrance generator 130. The controller 122 can be a specialized processing module of subsystem 120. Such processing modules are well-known in the art. Alternatively, the controller 122 can be a general data processor of the system 100. The controller 122 can receive the information indicative of the fragrance generation triggers in an example embodiment as data objects or messages conveyed from the application 110 to the fragrance subsystem 120 using standard data transmission mechanisms. The software-controllable switch 124 is a standard controllable switch for selectively applying a voltage or electrical current to a thermal element 134 of the fragrance generator 130 under direction of the controller 122.

In an example embodiment, the fragrance generator 130 includes a fragrance cartridge 132, a thermal element 134, and a thermal sensor 136. Under direction of controller 122, the thermal element 134 can be selectively activated to apply a pre-determined amount of heat to the fragrance cartridge 132. The amount of heat applied to the fragrance cartridge 132 can be varied by selectively applying different pre-determined voltage or electrical current levels to the fragrance cartridge 132. The amount of heat applied to the fragrance cartridge 132 can also be varied by selectively adjusting the length of time that heat is applied to the fragrance cartridge 132 by thermal element 134. In an example embodiment, the thermal element 134 can be a standard electrically activated thermal foil or other conventional electrically activated heating device.

Figure 2:
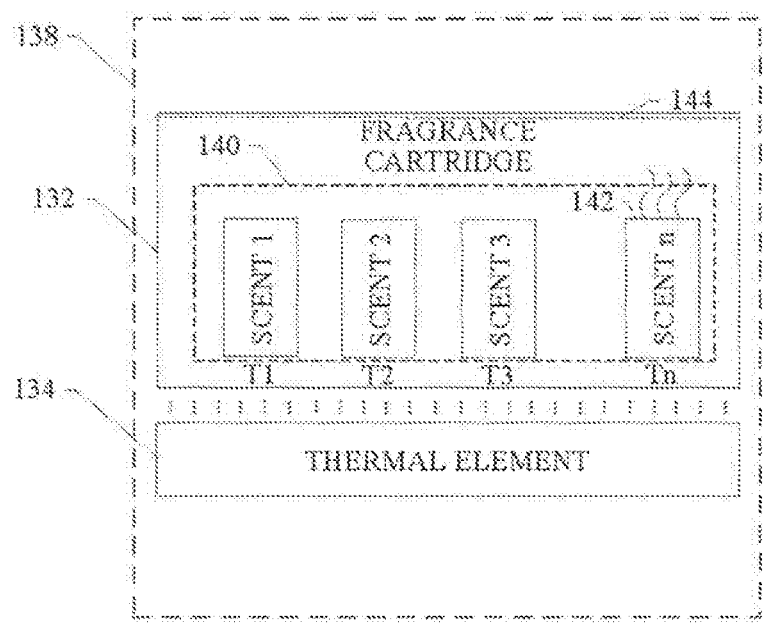
FIG. 2 illustrates an example embodiment of a fragrance cartridge having embedded thereon a plurality of fragrance regions.

FIG. 2 illustrates an example embodiment of a fragrance cartridge 132 having embedded thereon one or more fragrance regions 140. Referring now to FIG. 2, the fragrance cartridge 132 has embedded thereon one or more fragrance regions 140, which have each been saturated with a particular heat-activated scent formulation that vaporizes and emits a particular fragrance when the fragrance region 140 is heated to a pre-determined temperature by the thermal element 134. Such heat-activated scent formulations are well-known in the art. An example embodiment includes a plurality of fragrance regions 140, each being activated at a different temperature T1 to Tn. Thus, as the thermal element 134 heats the fragrance cartridge 132 to a temperature corresponding to Tn, the corresponding fragrance region (e.g., region 142 in this case) becomes active and the particular heat-activated scent formulation embedded on fragrance region 142 vaporizes emitting the particular fragrance. The emitted fragrance is allowed to escape the fragrance cartridge 132 via a vent 144.

Referring again to FIG. 1 in a particular embodiment, a thermal sensor 136 is included in the fragrance generator 130 to sense the temperature to which the thermal element 134 has been heated. Information indicative of the current temperature of thermal element 134 can be generated and transmitted to controller 122 by the thermal sensor 136. As a result, the thermal sensor 136 provides a useful feedback loop for the controller 122. This feedback loop enables the controller 122 to closely control the temperature of the fragrance cartridge 132 and thus closely control the specific fragrance emitted by the fragrance cartridge 132. This feedback loop also enables the controller 122 to monitor and control the temperature of the thermal element 134 and thereby prevent an overheat situation and maintain the safety of the system.

Figure 3:
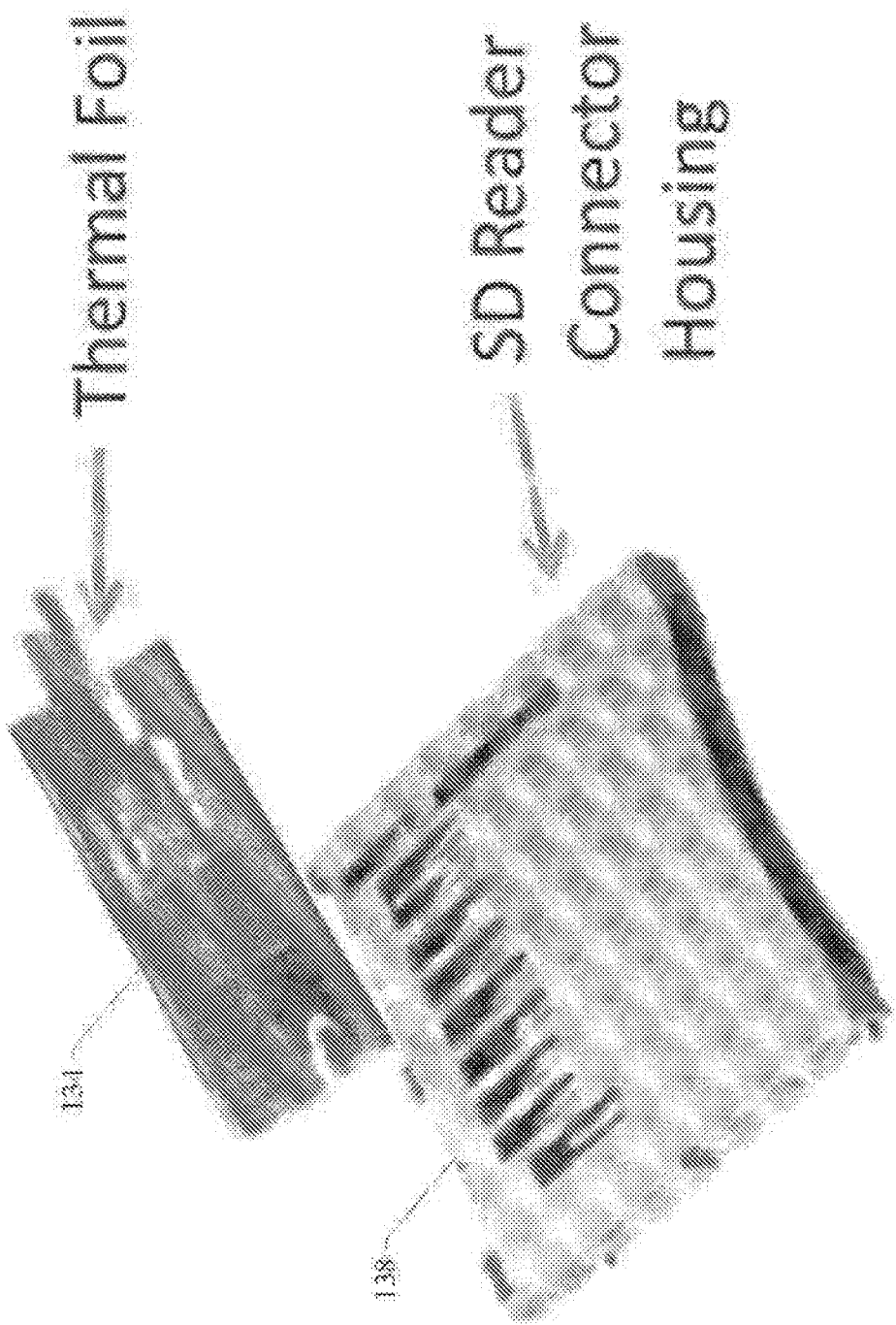
FIGS. 3 and 4 illustrate a particular embodiment of the fragrance generator configured for a Secure Digital (SD) card.
Figure 4:
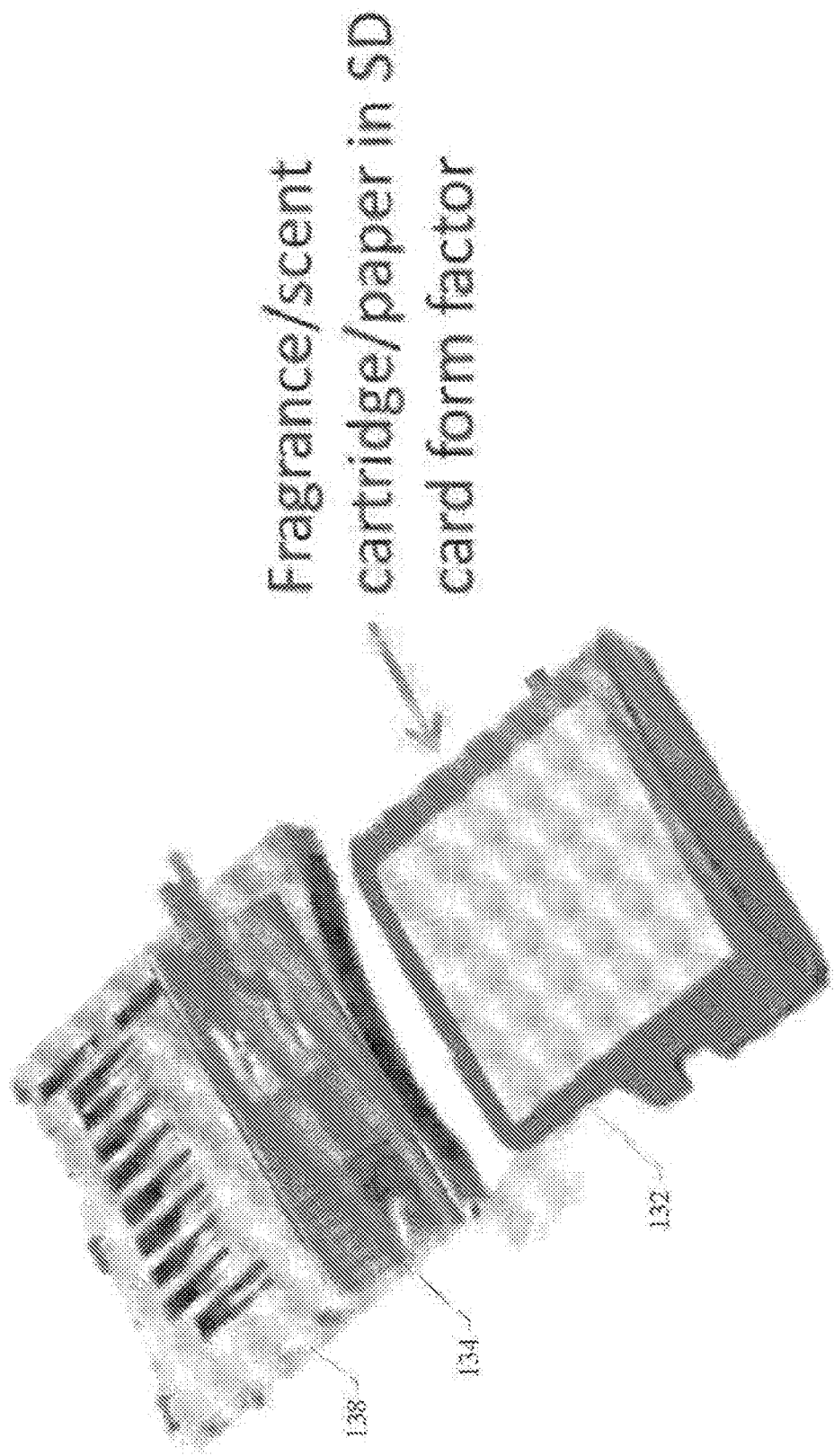

In a particular embodiment, the fragrance cartridge 132 can be configured to conform to the form factor of a Secure Digital (SD) card. A particular embodiment of the fragrance generator 130 configured for an SD card is illustrated in FIGS. 3 and 4. Referring to FIGS. 3 and 4, the fragrance cartridge 132 can be configured to the dimensions of a standard SD card form factor. As a result, the fragrance cartridge 132 can fit within a standard SD reader connector housing 138. The thermal element 134 can be embedded or inserted into the SD reader connector housing 138 for positioning proximate to the fragrance cartridge 132 when the fragrance cartridge 132 is inserted into the SD reader connector housing 138. As a result, the fragrance cartridge 132, configured as an SD card, can be inserted into a standard SD card slot on a computing platform or mobile device. This configuration allows a user to conveniently insert or remove a variety of different fragrances into or out of the SD card slot on the computing platform or mobile device. In a particular embodiment, a specially configured key or switch detection mechanism can be used on the SD card reader connector housing 138 to detect the insertion of either a standard SD card or a fragrance cartridge configured as an SD card. It will be apparent to those of ordinary skill in the art that the fragrance cartridge 132 and the fragrance generator 130 can be configured in a variety of different form factors as well.

As described herein, an example embodiment includes a fragrance generator coupled with a controller and a software-controllable switch for activating the fragrance generator. The controller can be triggered to activate the switch and the fragrance generator by an application program running on a computing platform or mobile device. The controller can also be triggered to activate the switch and the fragrance generator by inputs from various sensor devices, such as imaging devices, audio devices, infrared control devices, wireless devices, and the like. As a result, the application is capable of inserting olfactory stimuli into the operation of the application. For example, a game sequence may cause a game application to trigger the scent of gunpowder when a gun is fired. A photo viewing application can be configured to trigger the scent of flowers when an image of flowers is shown on a display screen. In this manner, a variety of scents can be triggered based on images shown or sounds heard as part of an application presentation. Similarly, sequences of fragrances can be triggered when a corresponding sequence is encountered in the operation of the application. For example, a character depicted in an application might be walking in a forest. In synchronous fashion, the application can use the embodiments described herein to trigger the fragrance of a forest to correspond to the character in the application. As the character continues to walk and arrives at the beach, the application can again use the embodiments described herein to trigger the fragrance of a beach to correspond to the current situation of the character in the application. In other embodiments, a sequence of scents can be generated and emitted according to the content of the text book, or electronic book (ebook). Thus, in a variety of applications, the embodiments described herein can enhance the user experience by enabling the application to add a variety of olfactory elements.

Figure 5:
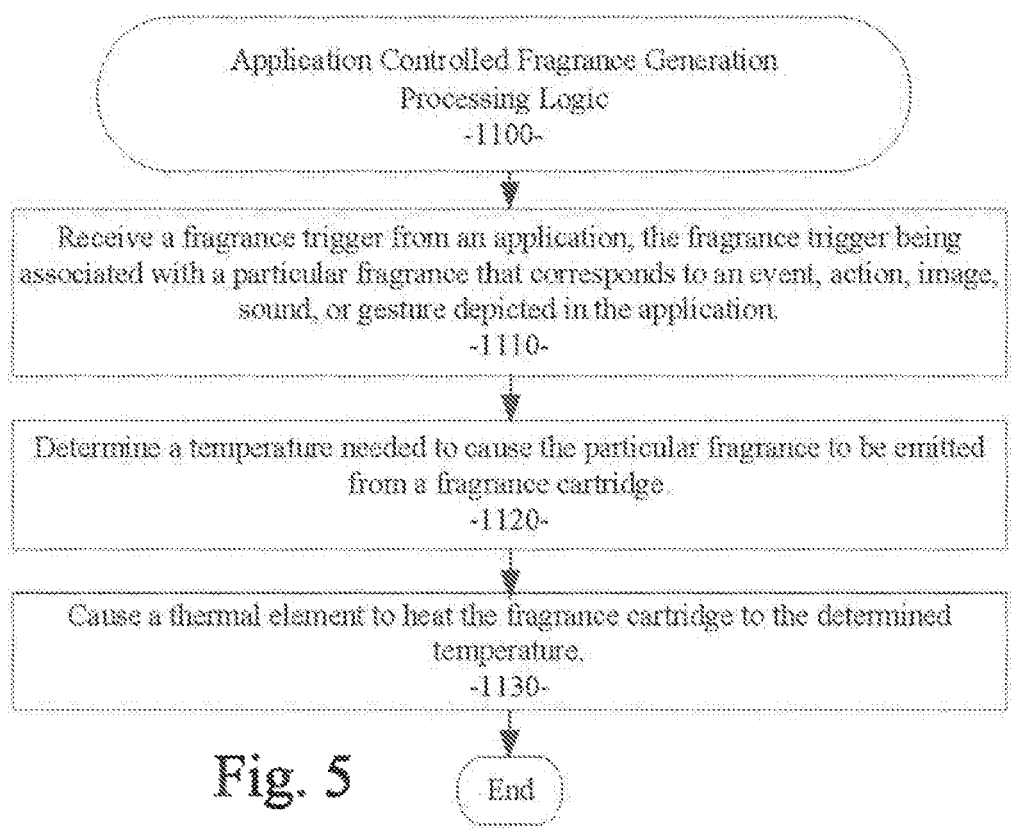
FIG. 5 is a processing flow chart illustrating an example embodiment of a method as described herein.

Referring now to FIG. 5 a processing flow diagram illustrates an example embodiment of a method 1100 for application controlled fragrance generation as described herein. The method 1100 of an example embodiment includes: receiving a fragrance trigger from an application, the fragrance trigger being associated with a particular fragrance that corresponds to an event, action, image, sound, or gesture depicted in the application (processing block 1110); determining a temperature needed to cause the particular fragrance to be emitted from a fragrance cartridge (processing block 1120); and causing a thermal element to heat the fragrance cartridge to the determined temperature (processing block 1130).

Figure 6:
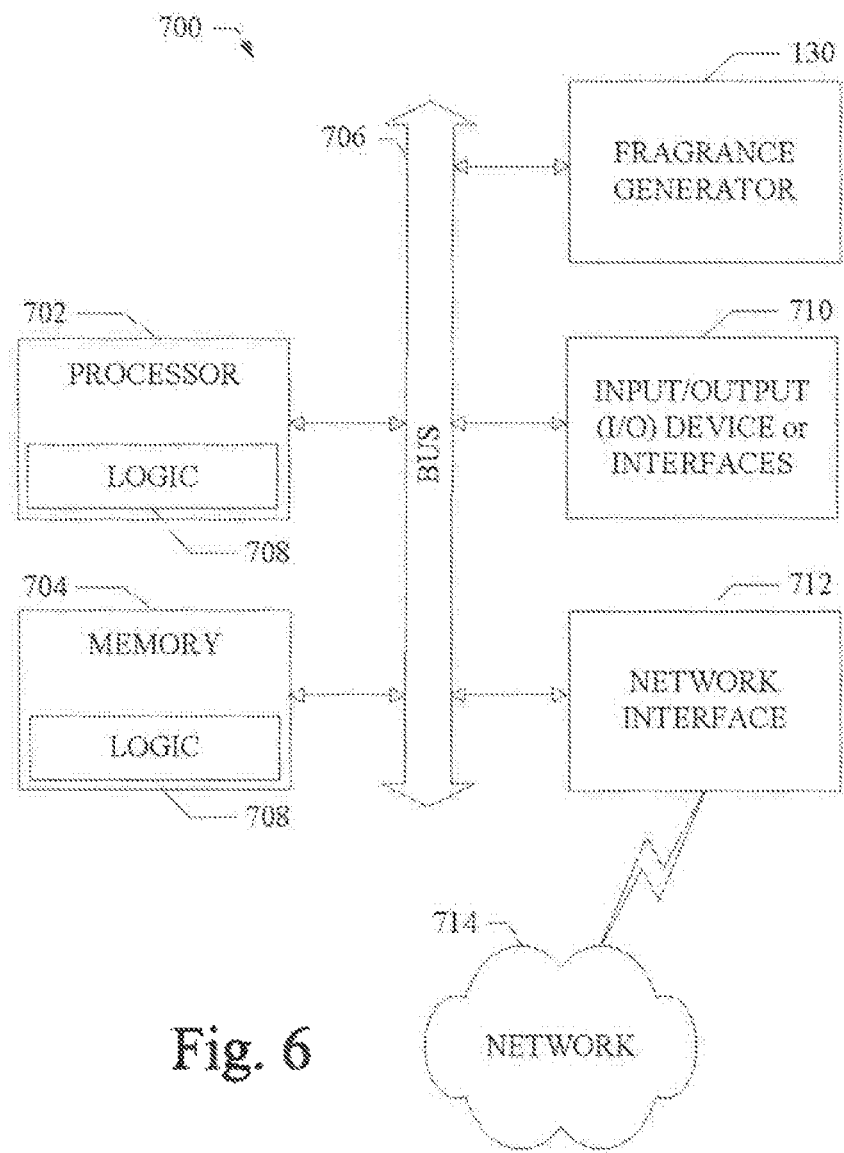
FIG. 6 shows a diagrammatic representation of a machine in the example form of a computing and/or communication system within which a set of instructions when executed and/or processing logic when activated may cause the machine to perform any one or more of the methodologies described and/or claimed herein.

FIG. 6 shows a diagrammatic representation of a machine in the example form of a mobile computing and/or communication system 700 within which a set of instructions when executed and/or processing logic when activated may cause the machine to perform any one or more of the methodologies described and/or claimed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a laptop computer, a tablet computing system, a Personal Digital Assistant (PDA), a cellular telephone, a smart phone, a web appliance, a set-top box (STB), a gaming console, a network router, switch or bridge, or any machine capable of executing a set of instructions (sequential or otherwise) or activating processing logic that specify actions to be taken by that machine. Further, while only a single machine is illustrated, the term "machine" can also be taken to include any collection of machines that individually or jointly execute a set (or multiple sets) of instructions or processing logic to perform any one or more of the methodologies described and/or claimed herein.

The example mobile computing and/or communication system 700 includes a data processor 702 (e.g., a System-on-a-Chip (SoC), general processing core, graphics core, and optionally other processing logic) and a memory 704, which can communicate with each other via a bus or other data transfer system 706. The mobile computing and/or communication system 700 may further include various input/output (I/O) devices and/or interfaces 710, such as a touch screen display, an audio jack, and optionally a network interface 712. In an example embodiment, the network interface 712 can include one or more radio transceivers configured for compatibility with any one or more standard wireless and/or cellular protocols or access technologies (e.g., 2nd (2G), 2.5, 3rd (3G), 4th (4G) generation, and future generation radio access for cellular systems, Global System for Mobile communication (GSM), General Packet Radio Services (GPRS), Enhanced Data GSM Environment (EDGE), Wideband Code Division Multiple Access (WCDMA), LTE, CDMA2000, WLAN, Wireless Router (WR) mesh, and the like). Network interface 712 may also be configured for use with various other wired and/or wireless communication protocols, including TCP/IP, UDP, SIP, SMS, RTP, WAP, CDMA, TDMA, UMTS, UWB, WiFi, WiMax, Bluetooth, IEEE 802.11x, and the like. In essence, network interface 712 may include or support virtually any wired and/or wireless communication mechanisms by which information may travel between the mobile computing and/or communication system 700 and another computing or communication system via network 714. Fragrance generator 130 includes the system components as described above in an example embodiment.

The memory 704 can represent a machine-readable medium on which is stored one or more sets of instructions, software, firmware, or other processing logic (e.g., logic 708) embodying any one or more of the methodologies or functions described and/or claimed herein. The logic 708, or a portion thereof, may also reside, completely or at least partially within the processor 702 during execution thereof by the mobile computing and/or communication system 700. As such, the memory 704 and the processor 702 may also constitute machine-readable media. The logic 708, or a portion thereof, may also be configured as processing logic or logic, at least a portion of which is partially implemented in hardware. The logic 708, or a portion thereof, may further be transmitted or received over a network 714 via the network interface 712. While the machine-readable medium of an example embodiment can be a single medium, the term "machine-readable medium" should be taken to include a single non-transitory medium or multiple non-transitory media (e.g., a centralized or distributed database, and/or associated caches and computing systems) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

In various embodiments as described herein, example embodiments include at least the following examples.

A fragrance generation subsystem comprising: a controller in data communication with an application; and a fragrance generator coupled to the controller, the fragrance generator including a fragrance cartridge and a thermal element, the fragrance cartridge emitting a selected fragrance when the thermal element is activated under control of the application.

The fragrance generation subsystem as above further including a software-controllable switch coupled between the controller and the fragrance generator for activating the thermal element of the fragrance generator under direction of the controller.

The fragrance generation subsystem as above wherein the application is configured to convey a fragrance trigger to the controller, the fragrance trigger corresponding to an event, action, image, sound, or gesture depicted in the application.

The fragrance generation subsystem as above wherein the application is configured to convey a fragrance trigger to the controller, the fragrance trigger corresponding to an input received from a sensor device of a type from the group consisting of: an imaging device, an audio device, an infrared control device, and a wireless device.

The fragrance generation subsystem as above wherein the fragrance cartridge is configured to have embedded thereon a plurality of fragrance regions.

The fragrance generation subsystem as above wherein the plurality of fragrance regions are each activated at a different temperature.

The fragrance generation subsystem as above further including a thermal sensor coupled between the controller and the thermal element to sense the temperature to which the thermal element has been heated.

The fragrance generation subsystem as above wherein the fragrance cartridge is configured to conform to the form factor of a Secure Digital (SD) card.

A system comprising: an application; a sensor device of a type from the group consisting of: an imaging device, an audio device, an infrared control device, and a wireless device, the sensor device being in data communication with the application, a controller in data communication with the application; and a fragrance generator coupled to the controller, the fragrance generator including a fragrance cartridge and a thermal element, the fragrance cartridge emitting a selected fragrance when the thermal element is activated under control of the application.

The system as above further including a software-controllable switch coupled between the controller and the fragrance generator for activating the thermal element of the fragrance generator under direction of the controller.

The system as above wherein the application is configured to convey a fragrance trigger to the controller, the fragrance trigger corresponding to an event, action, image, sound, or gesture depicted in the application.

The system as above wherein the application is configured to convey a fragrance trigger to the controller, the fragrance trigger corresponding to an input received from the sensor device.

The system as above wherein the fragrance cartridge is configured to have embedded thereon a plurality of fragrance regions.

The system as above wherein the plurality of fragrance regions are each activated at a different temperature.

The system as above further including a thermal sensor coupled between the controller and the thermal element to sense the temperature to which the thermal element has been heated.

The system as above wherein the fragrance cartridge is configured to conform to the form factor of a Secure Digital (SD) card.

A method comprising receiving a fragrance trigger from an application, the fragrance trigger being associated with a particular fragrance that corresponds to an event, action, image, sound, or gesture depicted in the application; determining, by a controller, a temperature needed to cause the particular fragrance to be emitted from a fragrance cartridge; and causing a thermal element to heat the fragrance cartridge to the determined temperature.

The method as above further including receiving a second fragrance trigger from the application, the second fragrance trigger being associated with a particular fragrance that corresponds to an input received from a sensor device of a type from the group consisting oft an imaging device, an audio device, an infrared control device, and a wireless device.

The method as above further including causing the thermal element to heat the fragrance cartridge to a plurality of different temperatures to cause the fragrance cartridge to emit a plurality of different fragrances.

The method as above further including sensing the temperature to which the thermal element has been heated.

An apparatus comprising, a controller means in data communication with an application; and a fragrance generation means coupled to the controller means, the fragrance generation means including a fragrance cartridge means and a heating means, the fragrance cartridge means emitting a selected fragrance when the heating means is activated under control of the application.

The apparatus as above further including a software-controllable switching means coupled between the controller means and the fragrance generation means for activating the heating means of the fragrance generation means under direction of the controller means.

The apparatus as above wherein the application is configured to convey a fragrance trigger to the controller means, the fragrance trigger corresponding to an event, action, image, sound, or gesture depicted in the application.

The apparatus as above wherein the application is configured to convey a fragrance trigger to the controller means, the fragrance trigger corresponding to an input received from a sensing means of a type from the group consisting of: an imaging device, an audio device, an infrared control device, and a wireless device.

The apparatus as above wherein the fragrance cartridge means is configured to have embedded thereon a plurality of fragrance regions.

The fragrance generation subsystem as above wherein the plurality of fragrance regions are each activated at a different temperature.

The apparatus as above further including a thermal sensing means coupled between the controller means and the heating means to sense the temperature to which the heating means has been heated.

The apparatus as above wherein the fragrance cartridge means is configured to conform to the form factor of a Secure Digital (SD) card.

A non-transitory machine-useable storage medium embodying instructions which, when executed by a machine, cause the machine to: receive a fragrance trigger from an application, the fragrance trigger being associated with a particular fragrance that corresponds to an event, action, image, sound, or gesture depicted in the application; determine a temperature needed to cause the particular fragrance to be emitted from a fragrance cartridge, and cause a thermal element to heat the fragrance cartridge to the determined temperature.

The machine-useable storage medium as above being further configured to receive a second fragrance trigger from the application, the second fragrance trigger being associated with a particular fragrance that corresponds to an input received from a sensor device of a type from the group consisting of an imaging device, an audio device, an infrared control device, and a wireless device.

The machine-useable storage medium as above being further configured to cause the thermal element to heat the fragrance cartridge to a plurality of different temperatures to cause the fragrance cartridge to emit a plurality of different fragrances.

The machine-useable storage medium as above being further configured to sense the temperature to which the thermal element has been heated.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A fragrance generation system comprising:
   a controller in data communication with an application, the application to convey a first fragrance trigger in response to a first image presented in the application at a first time to the controller, the application to convey a second fragrance trigger to the controller in response to a second image presented in the application at a second time different from the first time; and
   a fragrance generator in communication with the controller, the fragrance generator including a fragrance cartridge and a heater, the fragrance cartridge to emit (a) a first fragrance when the heater is activated in response to the first fragrance trigger during presentation of the first image, and (b) a second fragrance when the heater is activated in response to the second fragrance trigger during presentation of the second image.

2. The fragrance generation system of claim 1, further including a software-controllable switch in circuit with the controller and the fragrance generator to activate the heater of the fragrance generator under direction of the controller.

3. The fragrance generation system of claim 1, wherein the application is to convey a third fragrance trigger to the controller, the third fragrance trigger corresponding to an event, an action, a third image, a sound, or a gesture in the application.

4. The fragrance generation system of claim 1, wherein the first fragrance trigger corresponds to an input received from at least one of an imaging device, an audio device, an infrared control device, and a wireless device.

5. The fragrance generation system of claim 1, wherein the fragrance cartridge includes a plurality of fragrance regions.

6. The fragrance generation system of claim 5, wherein a first one of the fragrance regions is to be activated at a first temperature to emit the first fragrance and a second one of the fragrance regions is to be activated at a second temperature to emit the second fragrance.

7. The fragrance generation system of claim 1, further including a sensor to sense a temperature to which the heater has been heated.

8. The fragrance generation system of claim 1, wherein the fragrance cartridge is to conform to a form factor of a Secure Digital card.

9. The fragrance generation system of claim 1, wherein the controller is to adjust a length of time that the fragrance cartridge is to emit the first fragrance in response to the second fragrance trigger.

10. A method comprising:
    in response to a first fragrance trigger from an application, determining, by executing an instruction with a processor, a first temperature needed to cause a first fragrance to be emitted from a fragrance cartridge, the first fragrance trigger associated with a fragrance that corresponds to a first image presented in the application at a first time;
    causing, by executing an instruction with the processor, a thermal element to heat the fragrance cartridge to the first temperature to emit the first fragrance during presentation of the first image;
    in response to a second fragrance trigger from the application, determining, by executing an instruction with the processor, a second temperature needed to cause a second fragrance to be emitted from the fragrance cartridge, the second fragrance trigger associated with a fragrance that corresponds to a second image presented in the application at a second time different than the first time; and
    causing, by executing an instruction with the processor, the thermal element to transition from heating the fragrance cartridge at the first temperature to heating the fragrance cartridge at the second temperature to emit the second fragrance during presentation of the second image.

11. The method of claim 10, further including receiving a third fragrance trigger from the application, the third fragrance trigger associated with a third fragrance that corresponds to an input received from a sensor device.

12. The method of claim 10, wherein the first temperature is a first one of a plurality of different temperatures, the second temperature is a second one of the plurality of different temperatures, and further including causing the thermal element to heat the fragrance cartridge to the plurality of different temperatures to cause the fragrance cartridge to emit a plurality of different fragrances.

13. The method of claim 10, further including sensing thea temperature to which the thermal element has been heated.

14. At least one non-transitory machine-readable storage medium comprising instructions which, when executed by a machine, cause the machine to at least:
    in response to a first fragrance trigger from an application, determine a first temperature needed to cause a first fragrance to be emitted from a fragrance cartridge, the first fragrance trigger associated with a fragrance that corresponds to a first image presented in the application at a first time;
    cause a thermal element to heat the fragrance cartridge to the first temperature to emit the first fragrance during presentation of the first image;
    in response to a second fragrance trigger from the application, determine a second temperature needed to cause a second fragrance to be emitted from the fragrance cartridge, the second fragrance trigger associated with a fragrance that corresponds to a second image presented in the application at a second time different than the first time; and cause the thermal element to transition from heating the fragrance cartridge at the first temperature to heating the fragrance cartridge at the second temperature to emit the second fragrance during presentation of the second image.

15. The at least one storage machine-readable storage medium of claim 14, wherein the instructions cause the machine to respond to a third fragrance trigger from the application, the third fragrance trigger associated with a fragrance that corresponds to an input received from at least one of an imaging device, an audio device, an infrared control device, and a wireless device.

16. The at least one machine-readable storage medium of claim 14, wherein the instructions cause the machine to sense a temperature to which the thermal element has been heated.

17. The at least one machine-readable storage medium of claim 14, where the fragrance cartridge includes a plurality of fragrance regions.

18. The at least one machine-readable storage medium of claim 17, wherein the instructions cause the machine to activate a first fragrance region at the first temperature and a second fragrance region at the second temperature.

19. The at least one machine-readable storage medium of claim 14, wherein the instructions cause the machine to cause the thermal element to heat by causing a switch to close a circuit path to the thermal element.

20. The at least one machine-readable storage medium of claim 14, wherein the instructions cause the machine to adjust a length of time that the thermal element is to heat the fragrance cartridge at the first temperature in response to the second fragrance trigger.

* * * * *